(12) United States Patent
Tonouchi et al.

(10) Patent No.: US 12,123,742 B2
(45) Date of Patent: Oct. 22, 2024

(54) WALK DISCRIMINATION DEVICE, WALK DISCRIMINATION METHOD, AND PROGRAM RECORDING MEDIUM

(71) Applicant: NEC Corporation, Tokyo (JP)

(72) Inventors: Noriyuki Tonouchi, Tokyo (JP); Kazuki Ihara, Tokyo (JP); Chenhui Huang, Tokyo (JP); Kenichiro Fukushi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 496 days.

(21) Appl. No.: 17/436,210

(22) PCT Filed: Mar. 27, 2019

(86) PCT No.: PCT/JP2019/013347
§ 371 (c)(1),
(2) Date: Sep. 3, 2021

(87) PCT Pub. No.: WO2020/194598
PCT Pub. Date: Oct. 1, 2020

(65) Prior Publication Data
US 2022/0146280 A1 May 12, 2022

(51) Int. Cl.
*A61B 5/11* (2006.01)
*G01C 23/00* (2006.01)
(Continued)

(52) U.S. Cl.
CPC ............ *G01C 23/00* (2013.01); *A61B 5/1123* (2013.01); *G01D 1/12* (2013.01); *G01D 1/16* (2013.01); *G01D 1/18* (2013.01)

(58) Field of Classification Search
CPC ..... G01C 23/00; G01C 22/006; A61B 5/1123; A61B 5/107; A61B 5/11; G01D 1/12; G01D 1/16; G01D 1/18
See application file for complete search history.

(56) References Cited

U.S. PATENT DOCUMENTS

| 2011/0131005 A1* | 6/2011 | Ueshima ............ A63B 24/0087 |
| | | 73/488 |
| 2013/0123665 A1 | 5/2013 | Mariani et al. |

(Continued)

FOREIGN PATENT DOCUMENTS

| JP | 2009000391 A | * | 1/2009 | ........... A61B 5/1038 |
| JP | 2011245285 A | * | 12/2011 | |

(Continued)

OTHER PUBLICATIONS

International Search Report for PCT Application No. PCT/JP2019/013347, mailed on Jun. 25, 2019.
(Continued)

*Primary Examiner* — Eyob Hagos
(74) *Attorney, Agent, or Firm* — Sughrue Mion, PLLC

(57) ABSTRACT

A walk discrimination device includes: a data reception unit that receives sensor data including an acceleration and an angular velocity acquired by a sensor installed in a shoe; an acceleration determination unit that determines whether the acceleration included in the sensor data is positive or negative; an attitude angle calculation unit that calculates an attitude angle by use of the acceleration and the angular velocity included in the sensor data; an attitude angle determination unit that determines whether the attitude angle calculated by the attitude angle calculation unit has exceeded a threshold, and determines whether a peak of the attitude angle has been detected; a walk discrimination unit that discriminates a walk based on a determination order by the acceleration determination unit and the attitude angle determination unit; and an output unit that outputs a discrimination result by the walk discrimination unit.

8 Claims, 12 Drawing Sheets

(51) Int. Cl.
    *G01D 1/12*     (2006.01)
    *G01D 1/16*     (2006.01)
    *G01D 1/18*     (2006.01)

(56) References Cited

U.S. PATENT DOCUMENTS

| | | | |
|---|---|---|---|
| 2016/0030804 A1* | 2/2016 | Mizuochi | A61B 5/11 482/8 |
| 2018/0220937 A1* | 8/2018 | Mizuochi | A61B 5/112 |
| 2021/0302166 A1* | 9/2021 | Li | G01C 21/3617 |

FOREIGN PATENT DOCUMENTS

| | | | |
|---|---|---|---|
| JP | 2012-000343 A | | 1/2012 |
| JP | 2015017858 A | * | 1/2015 |
| JP | 2016-206903 A | | 12/2016 |
| JP | 2019-005340 A | | 1/2019 |
| WO | 2016/088842 A1 | | 6/2016 |
| WO | WO-2019008689 A1 | * | 1/2019 ............... A61B 5/11 |

OTHER PUBLICATIONS

English translation of Written opinion for PCT Application No. PCT/JP2019/013347, mailed on Jun. 25, 2019.

* cited by examiner

WALK DISCRIMINATION DEVICE, WALK DISCRIMINATION METHOD, AND PROGRAM RECORDING MEDIUM

This application is a National Stage Entry of PCT/JP2019/013347 filed on Mar. 27, 2019, the contents of all of which are incorporated herein by reference, in their entirety.

TECHNICAL FIELD

The present invention relates to a walk discrimination device, a walk discrimination method, and a program for measuring a walk on the basis of data acquired by a sensor attached to a foot portion.

BACKGROUND ART

With a growing interest in healthcare for physical condition management, a technique for counting the number of steps using sensor data acquired by a sensor attached to a foot portion has been developed.

PTL 1 discloses a step counting device that measures the number of steps of a pedestrian on the basis of acceleration data acquired by an acceleration sensor. The device of PTL 1 detects one of a foot-flat state in which a sole of a foot is in contact with a walking surface and a heel-off state in which a heel is away from the walking surface on the basis of the magnitude of an acceleration of a portion moving according to a walking movement. The device of PTL 1 detects whether the magnitude of the acceleration has exceeded a peak threshold. In the device of PTL 1, in a case where a second detector detects the magnitude of the acceleration exceeding the peak threshold after a start of the heel-off state is detected, it is determined that a movement of one step has been performed. The device of PTL 1 determines that the movement of one step of has been performed in a case where a first detector detects the foot-flat state after the second detector detects the magnitude of the acceleration exceeding the peak threshold.

CITATION LIST

Patent Literature

[PTL 1] JP 2016-206903 A

SUMMARY OF INVENTION

Technical Problem

The device of PTL 1 measures the number of steps of the pedestrian on the basis of the acceleration data acquired by the acceleration sensor. Therefore, the device of PTL 1 has a problem that a movement of the foot other than a walk, such as a movement of the foot in a sitting state or fidgeting of legs, is erroneously detected as a walk.

In order to solve the above-described problem, an object of the present invention is to provide a walk determination system capable of measuring a walk of a pedestrian in units of one step on the basis of sensor data.

Solution to Problem

A walk discrimination device according to one aspect of the present invention includes: a data reception unit that receives sensor data including an acceleration and an angular velocity acquired by a sensor installed in a shoe; an acceleration determination unit that determines whether the acceleration included in the sensor data is positive or negative; an attitude angle calculation unit that calculates an attitude angle by use of the acceleration and the angular velocity included in the sensor data; an attitude angle determination unit that determines whether the attitude angle calculated by the attitude angle calculation unit has exceeded a threshold, and determines whether a peak of the attitude angle has been detected; a walk discrimination unit that discriminates a walk based on a determination order by the acceleration determination unit and the attitude angle determination unit; and an output unit that outputs a discrimination result by the walk discrimination unit.

A walk discrimination method according to one aspect of the present invention includes: receiving sensor data including an acceleration and an angular velocity acquired by a sensor installed in a shoe; calculating an attitude angle by use of the acceleration and the angular velocity included in the sensor data; determining whether the attitude angle has exceeded a threshold; determining whether a negative peak of the attitude angle has been detected; determining whether the acceleration included in the sensor data is positive or negative; determining whether a positive peak of the attitude angle has been detected; and discriminating a walk based on a determination order.

A program according to one aspect of the present invention causes a computer to execute: processing of receiving sensor data including an acceleration and an angular velocity acquired by a sensor installed in a shoe; processing of calculating an attitude angle by use of the acceleration and the angular velocity included in the sensor data; processing of determining whether the attitude angle has exceeded a threshold; processing of determining whether a negative peak of the attitude angle has been detected; processing of determining whether the acceleration included in the sensor data is positive or negative; processing of determining whether a positive peak of the attitude angle has been detected; and processing of discriminating a walk based on a determination order.

Advantageous Effects of Invention

According to the present invention, it is possible to provide a walk determination system capable of measuring a walk of a pedestrian in units of one step on the basis of sensor data.

EXAMPLE EMBODIMENT

Figure 1:
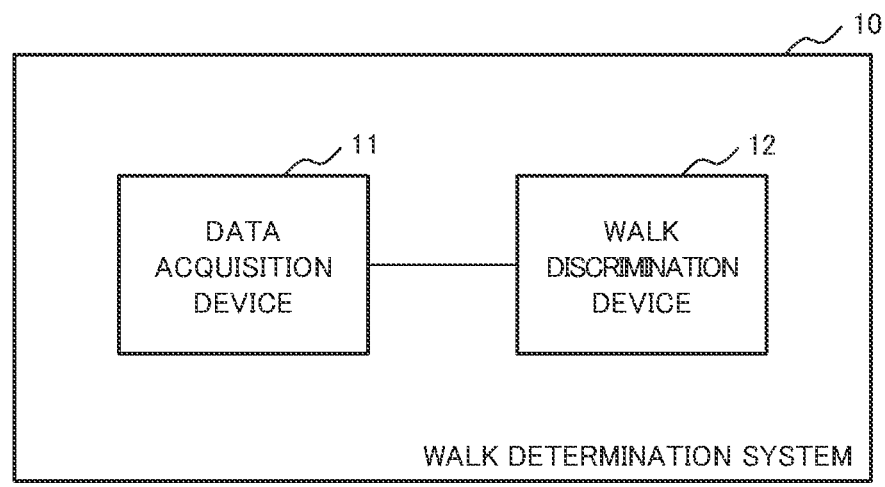
FIG. 1 is a block diagram illustrating an outline of a configuration of a walk determination system according to a first example embodiment of the present invention.

Hereinafter, example embodiments of the present invention will be described with reference to the drawings. However, although the example embodiments described below have technically preferable limitations for carrying out the present invention, the scope of the invention is not limited to the following. In all the drawings used in the following description of the example embodiments, the same reference signs are given to similar parts unless there is a particular reason. Furthermore, in the following example embodiments, repeated description of similar configurations and operations may be omitted. In addition, directions of arrows in the drawings are illustrative and do not limit directions of signals between blocks.

First Example Embodiment

First, a walk determination system according to a first example embodiment of the present invention will be described with reference to the drawings. The walk determination system of the present example embodiment calculates an attitude angle using sensor data acquired by an acceleration sensor and an angular velocity sensor installed in a shoe, and performs walk determination in units of one step on the basis of signal patterns of the attitude angle and an acceleration. In particular, the walk determination system of the present example embodiment performs the walk determination in units of one step by discriminating between sensor data measured in a state of sitting on a chair and sensor data measured by a walk.

FIG. 1 is a block diagram illustrating an outline of a configuration of a walk determination system 10 of the present example embodiment. The walk determination system 10 includes a data acquisition device 11 and a walk discrimination device 12. The data acquisition device 11 and the walk discrimination device 12 may be connected by wire or connected wirelessly.

The data acquisition device 11 includes at least an acceleration sensor and an angular velocity sensor. The data acquisition device 11 is installed in a shoe of a user. The data acquisition device 11 converts data acquired by the acceleration sensor and the angular velocity sensor into digital data (also referred to as sensor data), and transmits the converted sensor data to the walk discrimination device 12.

The data acquisition device 11 is implemented by, for example, an inertial measurement device including the acceleration sensor and the angular velocity sensor. An example of the inertial measurement device includes an inertial measurement unit (IMU). The IMU includes a three-axis acceleration sensor and angular velocity sensor. In addition, an example of the inertial measurement device includes a vertical gyro (VG). The VG has a configuration similar to that of the IMU, and can output a roll angle and a pitch angle with reference to a gravity direction by a method called strapdown. In addition, an example of the inertial measurement device includes an attitude heading reference system (AHRS). The AHRS has a configuration in which an electronic compass is added to the VG. The AHRS can output a yaw angle in addition to the roll angle and the pitch angle. Furthermore, an example of the inertial measurement device includes a global positioning system/inertial navigation system (GPS/INS). The GPS/INS has a configuration in which the GPS is added to the AHRS. The GPS/INS can calculate a position in a three-dimensional space in addition to the attitude angle (the roll angle, the pitch angle, and the yaw angle), and thus can estimate the position with high accuracy. The data acquisition device 11 calculates the attitude angle using the angular velocity sensor, and thus can be implemented by the IMU.

The walk discrimination device 12 calculates the attitude angle using the sensor data acquired by the data acquisition device 11. The attitude angle is an angle of a sole with respect to a horizontal plane. The walk discrimination device 12 discriminates a walk of the user using the attitude angle and the acceleration. The walk discrimination device 12 discriminates, on the basis of the sensor data acquired from the data acquisition device 11, whether the sensor data has been acquired in association with a walk of the user or in association with a movement other than a walk. Generally, in one step of walk, a lower limb is propelled in the order of lifting a toe off ground, accelerating and decelerating a leg swing (swing period), and grounding. As will be described later, the walk discrimination device 12 discriminates that one step of walk has been performed in response to a sequential detection of a negative peak of the attitude angle (lifting the toe off the ground), a positive acceleration (initial swing period), a negative acceleration (between middle swing period and terminal swing period), and a positive peak of the attitude angle (grounding).

The walk discrimination device 12 is implemented by, for example, software (application) or a circuit installed in a portable terminal device such as a smartphone, a mobile phone, a tablet, or a notebook personal computer. Furthermore, in a case where the walk discrimination device 12 is used for research data analysis or the like, for example, the walk discrimination device 12 may be implemented by software or a circuit installed in an information processing apparatus such as a stationary computer or a server.

Figure 2:
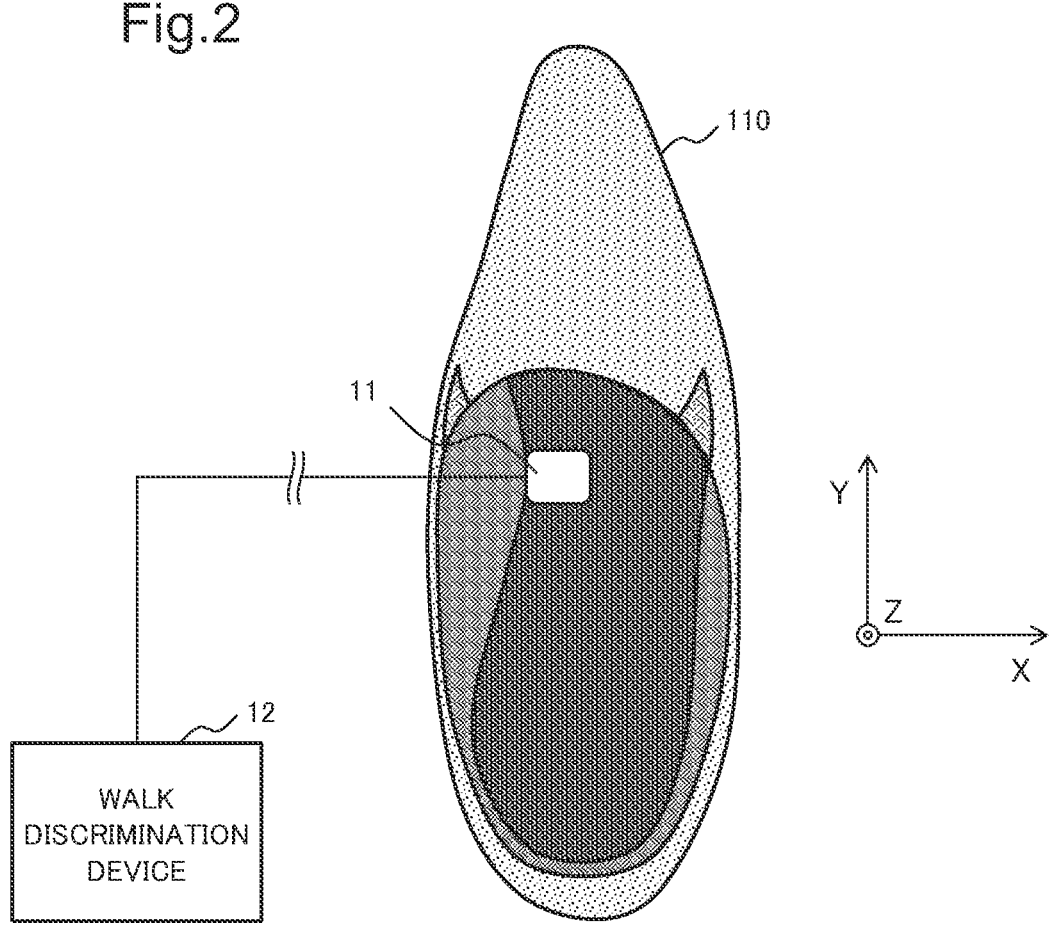
FIG. 2 is a conceptual diagram illustrating an arrangement example of a data acquisition device included in the walk determination system according to the first example embodiment of the present invention.

FIG. 2 is a conceptual diagram illustrating an example in which the data acquisition device 11 is installed in a shoe 110. In the example of FIG. 2, the data acquisition device 11 is installed at a position corresponding to a back side of an arch of the foot. In the present example embodiment, a lateral direction of a pedestrian is set to an X-axis direction (rightward direction is positive), a traveling direction of the pedestrian is set to a Y-axis direction (forward direction is positive), and the gravity direction is set to a Z-axis direction (vertically upward direction is positive).

The walk discrimination device 12 calculates the attitude angle using acceleration data and angular velocity data acquired by the data acquisition device 11. For example, the attitude angle is at least one of the roll angle (rotation around the Z axis), the pitch angle (rotation around the X axis), and the yaw angle (rotation around the Y axis). In the present example embodiment, as an example of the attitude angle, a walk is discriminated on the basis of the pitch angle (rotation around the X axis).

The outline of the configuration of the walk determination system 10 has been described above. Note that the configurations in FIGS. 1 and 2 are examples, and the configuration of the walk determination system 10 of the present example embodiment is not limited to these forms as they are.

[Data Acquisition Device]

Figure 3:
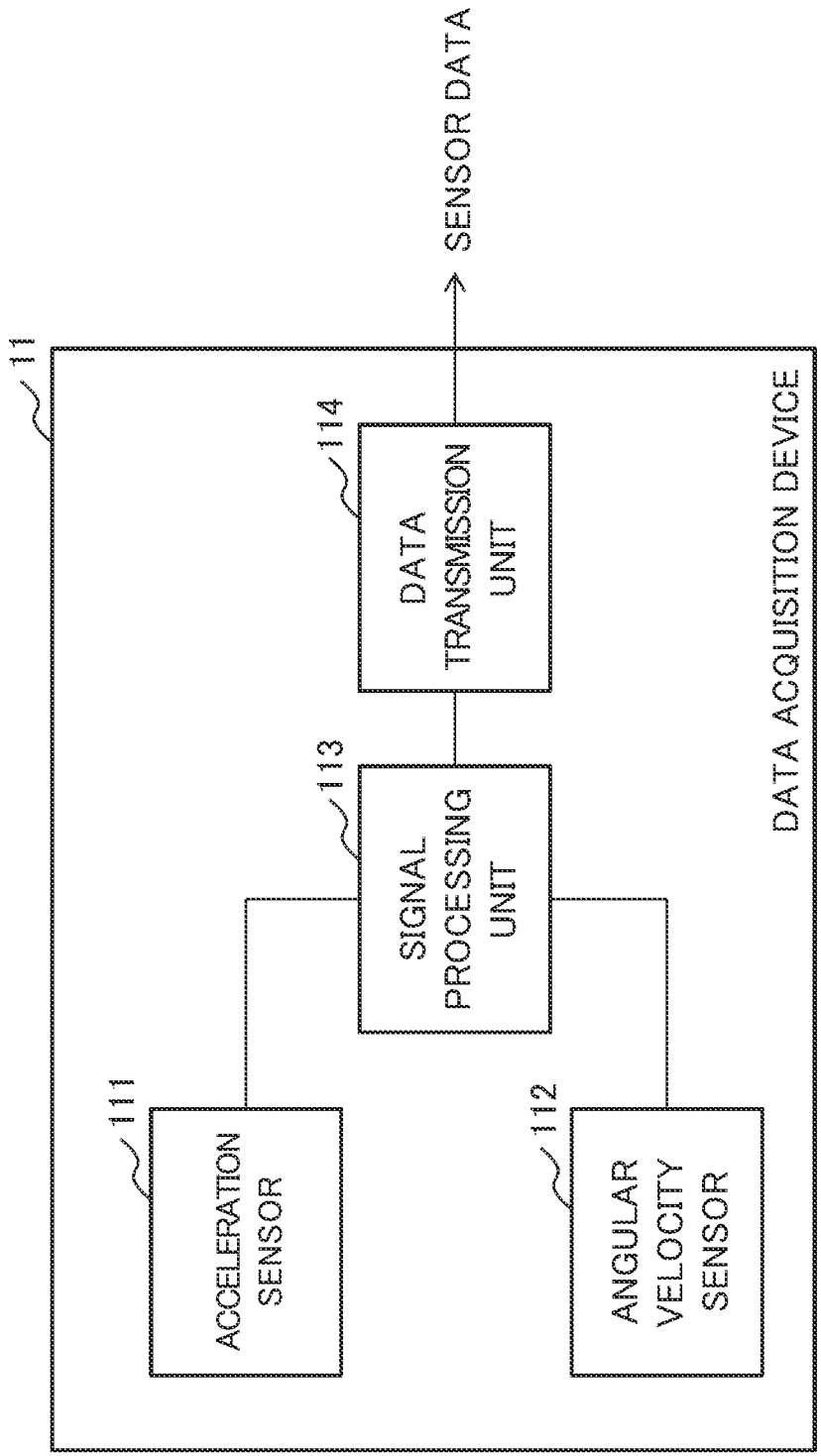
FIG. 3 is a block diagram illustrating an example of a configuration of the data acquisition device included in the walk determination system according to the first example embodiment of the present invention.

Next, the data acquisition device 11 included in the walk determination system 10 will be described with reference to FIG. 3. FIG. 3 is a block diagram illustrating an example of a configuration of the data acquisition device 11. The data acquisition device 11 includes an acceleration sensor 111, an angular velocity sensor 112, a signal processing unit 113, and a data transmission unit 114.

The acceleration sensor 111 is a sensor that measures an acceleration in three axial directions. The acceleration sensor 111 outputs the measured acceleration to the signal processing unit 113.

The angular velocity sensor 112 is a sensor that measures an angular velocity. The angular velocity sensor 112 outputs the measured angular velocity to the signal processing unit 113.

The signal processing unit 113 acquires the acceleration and the angular velocity from the acceleration sensor 111 and the angular velocity sensor 112, respectively. The signal processing unit 113 converts the acquired acceleration and angular velocity into digital data, and outputs the converted digital data (sensor data) to the data transmission unit 114. The sensor data includes at least acceleration data obtained by converting the acceleration of analog data into digital data and angular velocity data obtained by converting the angular velocity of analog data into digital data. Note that the sensor data may include an acquisition time of raw data of the acceleration and the angular velocity. In addition, the signal processing unit may be configured to output sensor data obtained by performing correction such as correction of a mounting error, temperature correction, or linearity correction on the acquired raw data of the acceleration and the angular velocity.

The data transmission unit 114 acquires the sensor data from the signal processing unit 113. The data transmission unit 114 transmits the acquired sensor data to the walk discrimination device 12. The data transmission unit 114 may transmit the sensor data to the walk discrimination device 12 via a wire such as a cable, or may transmit the sensor data to the walk discrimination device 12 via wireless communication. For example, the data transmission unit 114 may be configured to transmit the sensor data to the walk discrimination device 12 via a wireless communication function (not illustrated) conforming to a standard such as Bluetooth (registered trademark) or WiFi (registered trademark).

The example of the configuration of the data acquisition device 11 has been described above. Note that the configuration in FIG. 3 is an example, and the configuration of the data acquisition device 11 included in the walk determination system 10 of the present example embodiment is not limited to this form as it is.

[Walk Discrimination Device]

Figure 4:
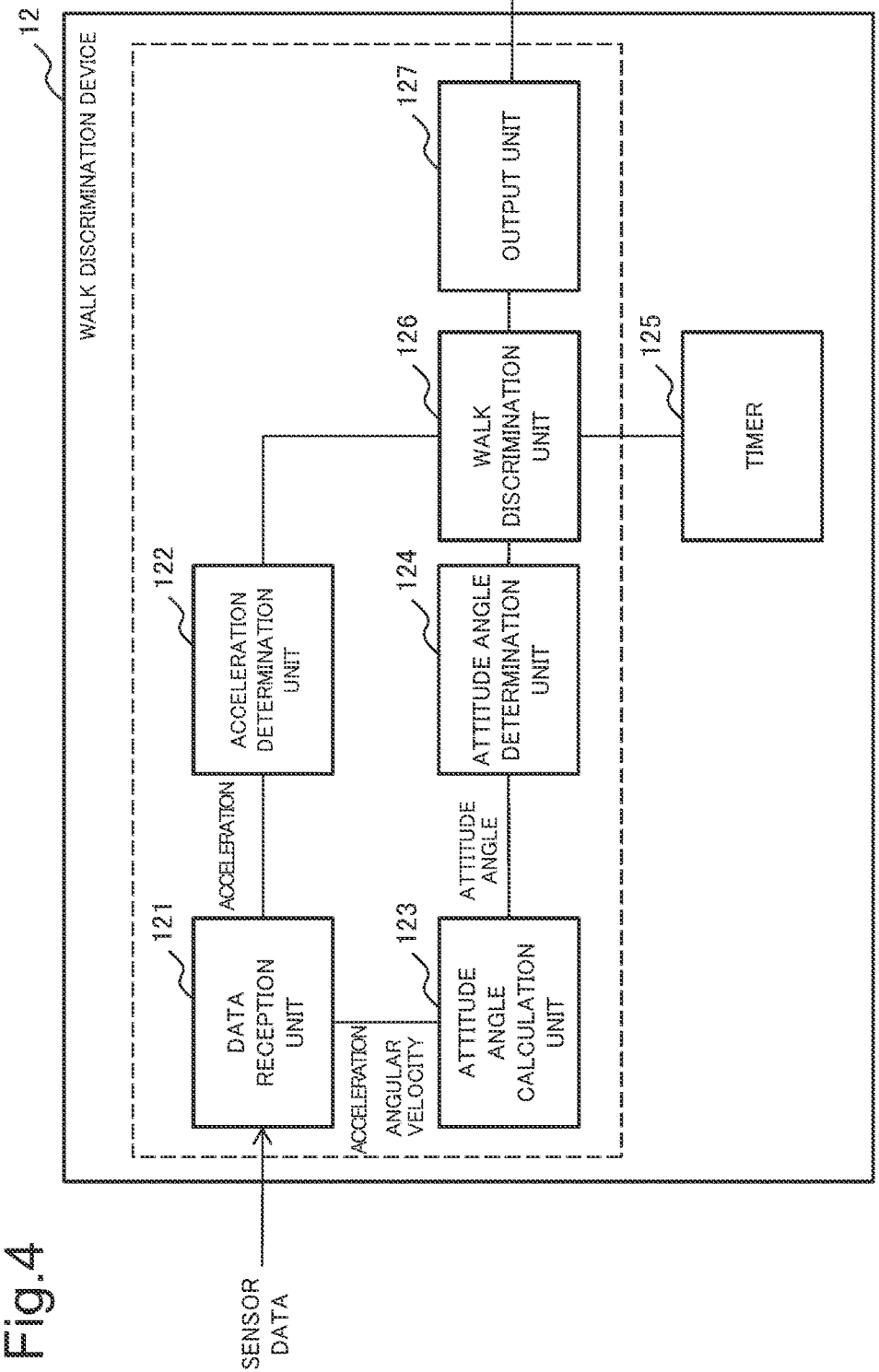
FIG. 4 is a block diagram illustrating an example of a configuration of a walk discrimination device included in the walk determination system according to the first example embodiment of the present invention.

Next, the walk discrimination device 12 included in the walk determination system 10 will be described with reference to FIGS. 4 to 6. FIG. 4 is a block diagram illustrating an example of a configuration of the walk discrimination device 12. The walk discrimination device 12 includes a data reception unit 121, an acceleration determination unit 122, an attitude angle calculation unit 123, an attitude angle determination unit 124, a timer 125, a walk discrimination unit 126, and an output unit 127.

The data reception unit 121 acquires the sensor data from the data acquisition device 11. The data reception unit 121 outputs the acceleration data included in the sensor data to the acceleration determination unit 122, and outputs the acceleration data and the angular velocity data included in the sensor data to the attitude angle calculation unit 123.

The acceleration determination unit 122 acquires the acceleration data from the data reception unit 121. The acceleration determination unit 122 determines whether the acquired acceleration is positive or negative. The acceleration determination unit 122 outputs a determination result as to whether the acceleration is positive or negative to the walk discrimination unit 126. For example, the acceleration determination unit 122 outputs a positive signal (also referred to as a first acceleration signal) in a case where the acceleration is positive, and outputs a negative signal (also referred to as a second acceleration signal) in a case where the acceleration is negative.

The attitude angle calculation unit 123 acquires the acceleration data and the angular velocity data from the data reception unit 121. The attitude angle calculation unit 123 calculates the attitude angle using the acquired acceleration data and angular velocity data. The attitude angle calculation unit 123 outputs the calculated attitude angle to the attitude angle determination unit 124.

The attitude angle determination unit 124 acquires the attitude angle from the attitude angle calculation unit 123. The attitude angle determination unit 124 determines whether the acquired attitude angle has exceeded a threshold. In a case where the attitude angle exceeds the threshold, the attitude angle determination unit 124 outputs an over-threshold signal indicating that the attitude angle has exceeded the threshold to the walk discrimination unit 126.

The attitude angle determination unit 124 detects the negative peak and the positive peak of the attitude angle. If detecting the negative peak of the attitude angle, the attitude angle determination unit 124 outputs, to the walk discrimination unit 126, a negative peak signal (also referred to as a first attitude angle signal) indicating that the negative peak has been detected. If detecting the positive peak of the attitude angle, the attitude angle determination unit 124 outputs, to the walk discrimination unit 126, a positive peak signal (also referred to as a second attitude angle signal) indicating that the positive peak has been detected.

The timer 125 adds time to the signals received by the walk discrimination unit 126. The walk discrimination unit 126 can discriminate, according to the time added by the timer 125, the order in which the over-threshold signal, the negative peak signal, the positive signal, the negative signal, and the positive peak signal are received. In a case where the acquisition time of the data is added to the sensor data, the order of the signals can be discriminated on the basis of the acquisition time, and thus the timer 125 can be omitted. In FIG. 4, a configuration in a broken line frame corresponds to a configuration in which the timer 125 is omitted.

The walk discrimination unit 126 receives the positive signal and the negative signal from the acceleration determination unit 122. The walk discrimination unit 126 receives the over-threshold signal, the negative peak signal, and the positive peak signal from the attitude angle determination unit 124. The walk discrimination unit 126 discriminates whether one step of walk has been performed on the basis of the order of receiving the over-threshold signal, the negative peak signal, the positive signal, the negative signal, and the positive peak signal. The walk discrimination unit 126 outputs a discrimination result to the output unit 127.

Figure 5:
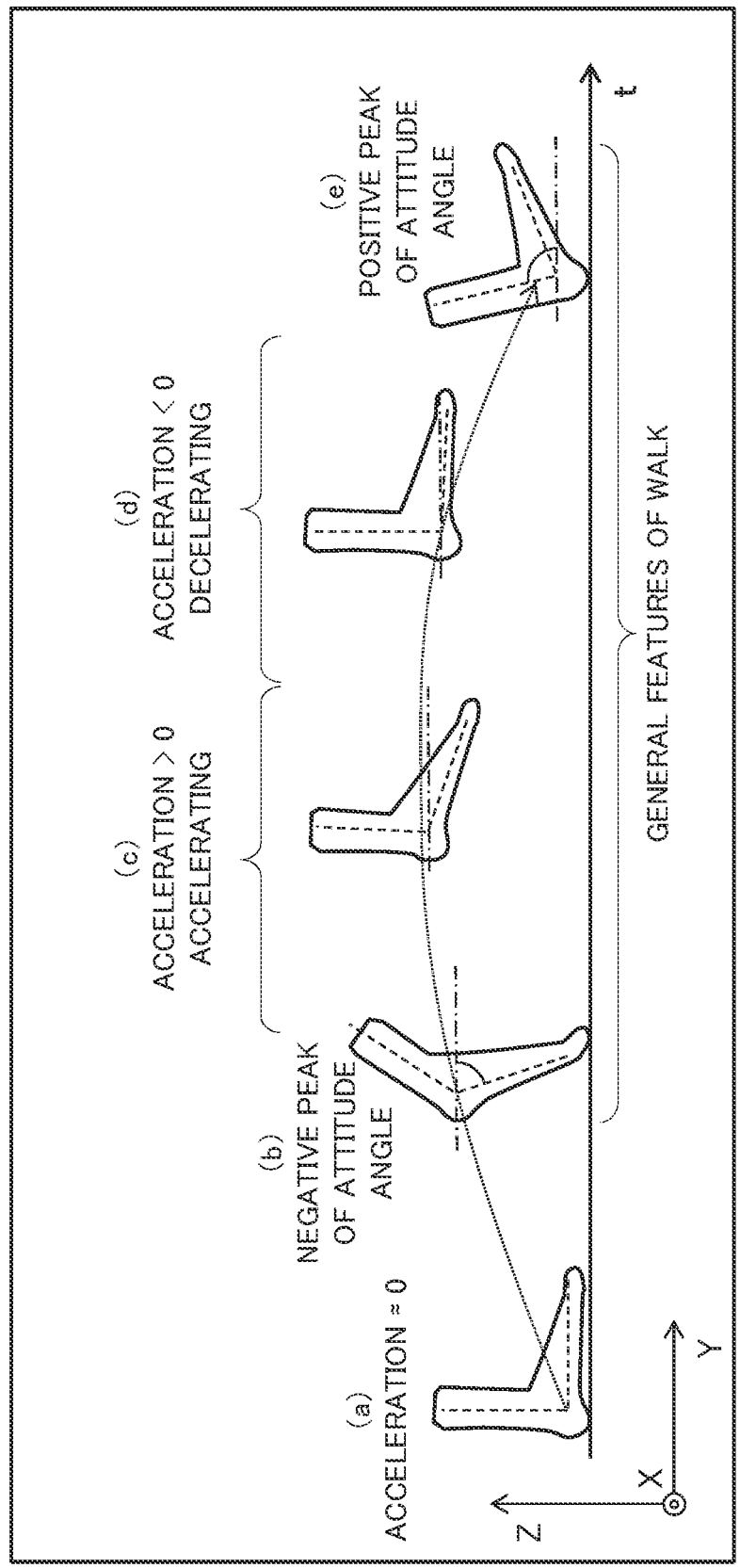
FIG. 5 is a conceptual diagram for describing general features of a walk.

FIG. 5 is a conceptual diagram for describing general features of a walk. In a case where the user is not walking, the acceleration is substantially zero (a) unless the foot is moved. In a case where the user is walking, the negative peak of the attitude angle (b), the positive acceleration (c), the negative acceleration (d), and the positive peak of the attitude angle (e) are detected sequentially after the attitude angle exceeds the threshold. At this time, the walk discrimination unit 126 discriminates that one step of walk has been performed in response to a sequential detection of the over-threshold signal, the negative peak signal, the positive signal, the negative signal, and the positive peak signal.

Figure 6:
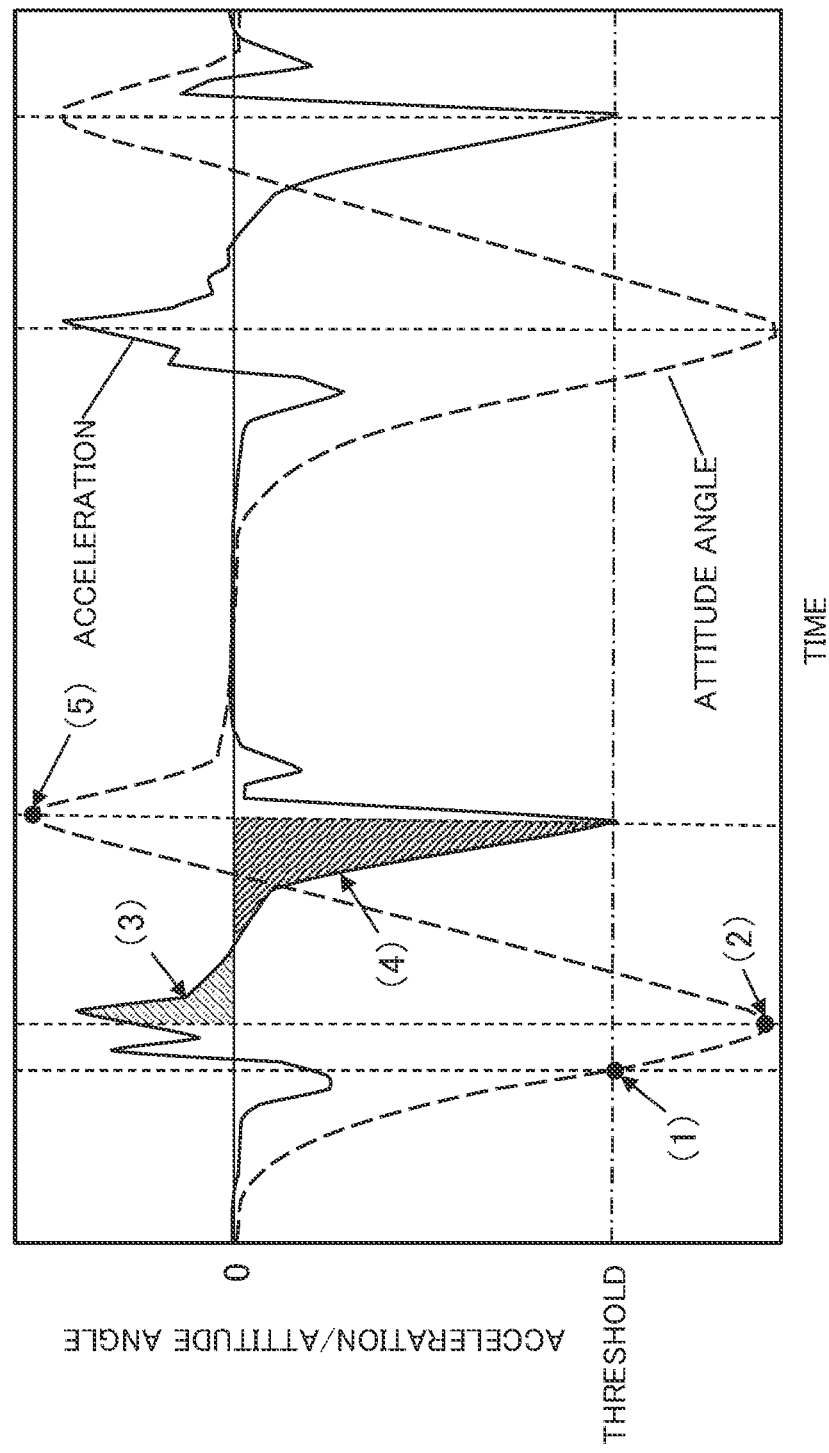
FIG. 6 is a graph for describing walk determination performed by the walk determination system according to the first example embodiment of the present invention.

FIG. 6 is a graph in which the acceleration (solid line) received by the walk discrimination device 12 and the attitude angle (broken line) calculated by the walk discrimination device 12 are put together. In the graph of FIG. 6, a horizontal axis represents time, and a vertical axis represents the acceleration and the attitude angle. The graph of FIG. 6 is for describing a relationship between temporal changes of the acceleration and the attitude angle, and a specific scale is omitted.

After detecting the attitude angle having exceeded the threshold (1), the walk discrimination device 12 detects the negative peak of the attitude angle (2). In the example of FIG. 6, as time passes, the attitude angle exceeds the threshold in a negative direction. If detecting the negative peak of the attitude angle (2), the walk discrimination device 12 detects whether the acceleration is positive or negative. At this time, the walk discrimination device 12 discriminates that one step of walk has been performed when the walk discrimination device 12 detects the acceleration changing in the order of positive (3) and negative (4) and the positive peak of the attitude angle (5).

The output unit 127 acquires the discrimination result as to whether one step of walk has been performed from the walk discrimination unit 126. The output unit 127 outputs the acquired discrimination result. For example, the output unit 127 outputs the discrimination result as to whether one step of walk has been performed to a step counting device or a step counting program that measures the number of steps on the basis of the discrimination result. Furthermore, for example, the output unit 127 outputs the discrimination result as to whether one step of walk has been performed to a display device that displays the discrimination result. Note that the output destination of the discrimination result is not limited to the step counting device or the display device as long as the output destination is a device or a program using the discrimination result.

The example of the configuration of the walk discrimination device 12 has been described above. Note that the configuration in FIG. 4 is an example, and the configuration of the walk discrimination device 12 included in the walk determination system 10 of the present example embodiment is not limited to this form as it is.

(Operation)

Figure 7:
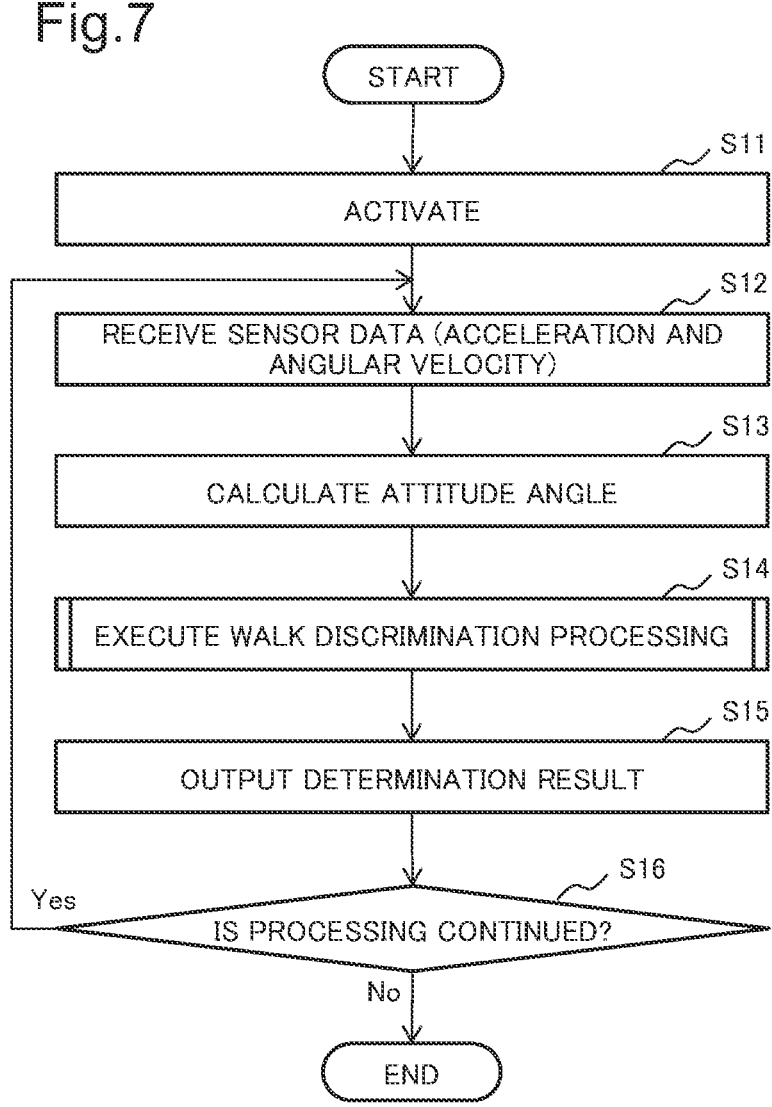
FIG. 7 is a flowchart for describing an operation of the walk discrimination device included in the walk determination system according to the first example embodiment of the present invention.

Next, an operation of the walk discrimination device 12 of the present example embodiment will be described with reference to FIG. 7. FIG. 7 is a flowchart for describing the operation of the walk discrimination device 12.

In FIG. 7, first, the walk discrimination device 12 is activated (step S11).

Next, the walk discrimination device 12 receives the sensor data (the acceleration and the angular velocity) from the data acquisition device 11 (step S12).

Next, the walk discrimination device 12 calculates the attitude angle using the acceleration and the angular velocity included in the received sensor data (step S13).

Next, the walk discrimination device 12 executes walk discrimination processing (step S14).

Next, the walk discrimination device 12 outputs the discrimination result (step S15).

If the processing is continued, the processing returns to step S12. If the processing is ended, the processing along the flowchart of FIG. 7 is ended.

The operation of the walk discrimination device 12 has been described above. Note that the flowchart of FIG. 7 is an example, and the operation of the walk discrimination device 12 of the present example embodiment is not limited to this procedure as it is.

[Walk Discrimination Processing]

Figure 8:
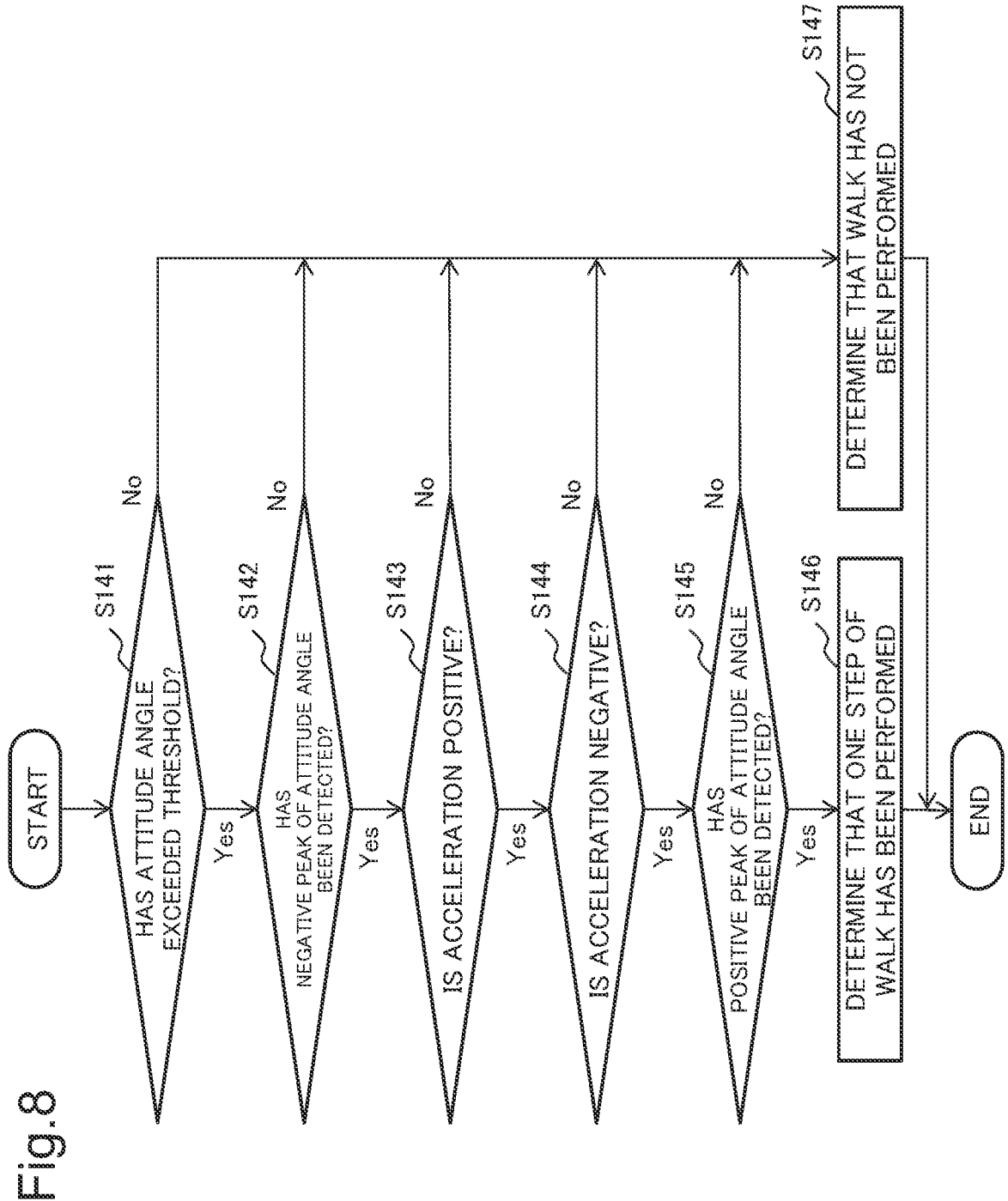
FIG. 8 is a flowchart for describing walk discrimination processing by the walk discrimination device included in the walk determination system according to the first example embodiment of the present invention.

Next, the walk discrimination processing by the walk discrimination device 12 of the present example embodiment will be described with reference to FIG. 8. FIG. 8 is a flowchart for describing the walk discrimination processing by the walk discrimination device 12.

In FIG. 8, first, the walk discrimination device 12 determines whether the attitude angle has exceeded the threshold (step S141). If the attitude angle exceeds the threshold (Yes in step S141), the processing proceeds to step S142. On the other hand, if the attitude angle does not exceed the threshold (No in step S141), the walk discrimination device 12 determines that a walk has not been performed (step S147).

Next, the walk discrimination device 12 determines whether the negative peak of the attitude angle has been detected (step S142). If the negative peak of the attitude angle is detected (Yes in step S142), the processing proceeds to step S143. On the other hand, if the negative peak of the attitude angle is not detected (No in step S142), the walk discrimination device 12 determines that a walk has not been performed (step S147).

Next, the walk discrimination device 12 determines whether the acceleration is positive (step S143). If the acceleration is positive (Yes in step S143), the processing proceeds to step S144. On the other hand, if the acceleration is not positive (No in step S143), the walk discrimination device 12 determines that a walk has not been performed (step S147).

Next, the walk discrimination device 12 determines whether the acceleration has changed to negative (step S144). If the acceleration has changed to negative (Yes in step S144), the processing proceeds to step S145. On the other hand, if the acceleration does not change to negative (No in step S144), the walk discrimination device 12 determines that a walk has not been performed (step S147).

Next, the walk discrimination device 12 determines whether the positive peak of the attitude angle has been detected (step S145). If the positive peak of the attitude angle is detected (Yes in step S145), the walk discrimination device 12 determines that one step of walk has been performed (step S146). On the other hand, if the positive peak of the attitude angle is not detected (No in step S145), the walk discrimination device 12 determines that a walk has not been performed (step S147).

The walk discrimination processing by the walk discrimination device 12 has been described above. Note that the processing along the flowchart of FIG. 8 is an example, and the walk discrimination processing by the walk discrimination device 12 of the present example embodiment is not limited to this procedure as it is.

For example, a series of processing by the walk discrimination device 12 is executed as routine processing at a start of a walk measurement. The series of processing by the walk discrimination device 12 may be added between normal walk measurements. The series of processing by the walk discrimination device 12 may be added for each step in step count in the walk measurement.

As described above, a walk determination system of the present example embodiment includes a walk discrimination device including a data reception unit, an acceleration determination unit, an attitude angle calculation unit, an attitude angle determination unit, a walk discrimination unit, and an output unit. The data reception unit receives sensor data including an acceleration and an angular velocity acquired by a sensor installed in a shoe. The acceleration determination unit determines whether the acceleration included in the sensor data is positive or negative. The attitude angle calculation unit calculates an attitude angle using the acceleration and the angular velocity included in the sensor data. The attitude angle determination unit determines whether the attitude angle calculated by the attitude angle calculation unit has exceeded a threshold, and determines whether a peak of the attitude angle has been detected. The walk discrimination unit discriminates a walk on the basis of a determination order by the acceleration determination unit and the attitude angle determination unit. The output unit outputs a discrimination result by the walk discrimination unit.

In one aspect of the present example embodiment, the acceleration determination unit outputs a first acceleration signal in a case where the acceleration included in the sensor data is positive, and outputs a second acceleration signal in a case where the acceleration included in the sensor data is negative. The attitude angle determination unit outputs an over-threshold signal when the attitude angle exceeds the threshold. Furthermore, the attitude angle determination unit outputs a first attitude angle signal when a negative peak of the attitude angle is detected, and outputs a second attitude angle signal when a positive peak of the attitude angle is detected.

In one aspect of the present example embodiment, the walk discrimination unit determines that a walk has been performed when the walk discrimination unit sequentially receives the first attitude angle signal, the first acceleration signal, the second acceleration signal, and the second attitude angle signal after the over-threshold signal is received. In addition, in one aspect of the present example embodiment, the walk discrimination unit determines that one step of walk has been performed when the walk discrimination unit sequentially receives the first attitude angle signal, the first acceleration signal, the second acceleration signal, and the second attitude angle signal after the over-threshold signal is received.

In one aspect of the present example embodiment, the walk discrimination device includes a timer that supplies time data to the walk discrimination unit. The walk discrimination unit discriminates an order of the first attitude angle signal, the first acceleration signal, the second acceleration signal, and the second attitude angle signal on the basis of the time data supplied by the timer.

Figure 9:
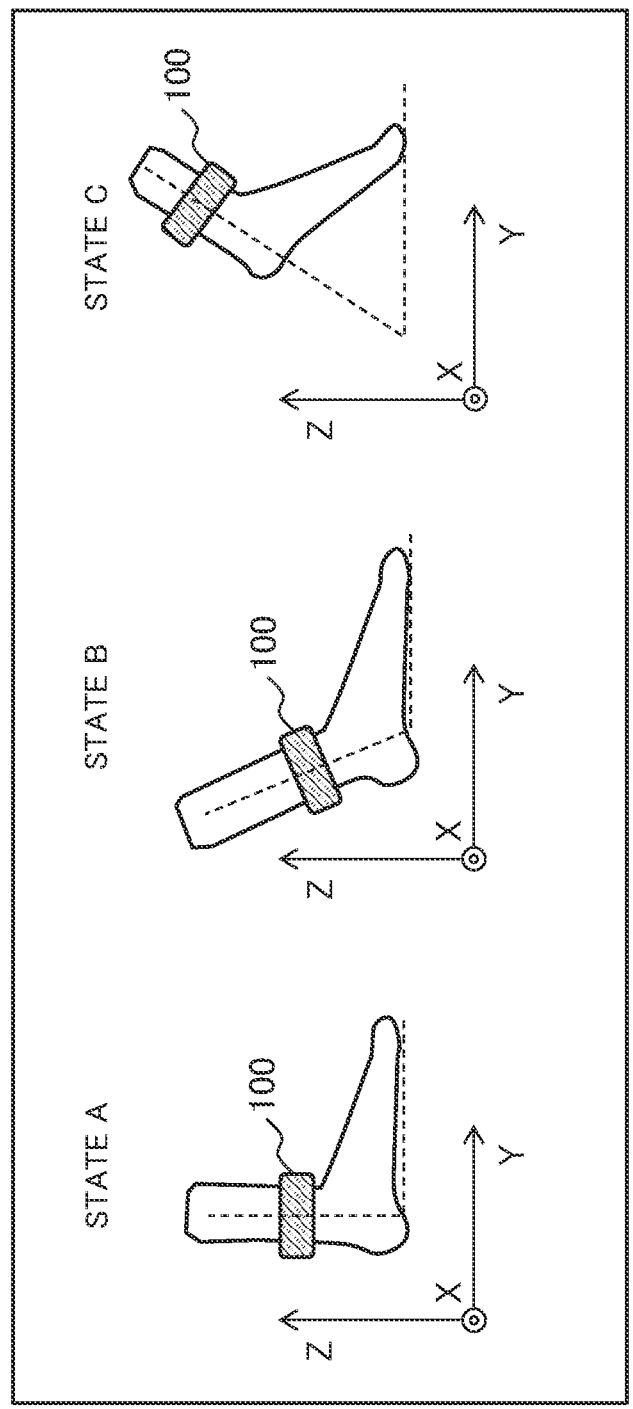
FIG. 9 is a conceptual diagram illustrating an example of a state of a foot when a person is sitting on a chair.

FIG. 9 is a conceptual diagram for describing an example in which a walk is erroneously detected when the user is sitting on a chair with a sensor 100 attached to an ankle. A state A is a state in which the sole is in contact with the ground and a shin is perpendicular to the ground. A state B is a state in which the sole is in contact with the ground and the shin is inclined with respect to the ground. A state C is a state in which a heel is separated from the ground and the shin is inclined with respect to the ground. In daily life, state changes between the state A, the state B, and the state C frequently occur. For example, state changes such as the state A to the state B, the state C to the state A, and the state C to the state B are behaviors similar to a walk, and thus may be erroneously detected as a walk.

In order to prevent erroneous detection of a walk detected in a sitting state, the threshold of the acceleration or the angular velocity can be set high, but when the threshold is set too high, there is a possibility that omission in detecting a walk may occur in a slow walk or the like. In addition, when an axis with respect to the ground deviates from an initial position due to the influence of gravity, the acceleration sensor is in a state in which an offset is added. Therefore, in the case where the angle of the sensor deviates from the initial state, the offset is always added to the acceleration, and it becomes difficult to discriminate a state in which the foot is grounded to the ground (a state within the threshold).

In the method of the present example embodiment, the attitude angle information is added to the increase and decrease in the acceleration of the foot portion, which accompany the leg swing, so that a walk is discriminated on the basis of a physical quantity reflecting a walking movement, and thus the erroneous detection is reduced. That is, according to the present example embodiment, it is possible to provide a walk determination system capable of measuring a walk of a pedestrian in units of one step on the basis of sensor data.

In addition, according to the method of the present example embodiment, a walk in going up and down an inclined road or a staircase can be excluded, and a walk on a flat road can be discriminated. Therefore, the method of the present example embodiment is suitable for healthcare that manages a physical condition of a user by daily recording and comparing a walk of the user on a flat road in ordinary time.

Second Example Embodiment

Next, a walk determination system according to a second example embodiment of the present invention will be described with reference to the drawings. The walk determination system of the present example embodiment is different from that of the first example embodiment in a part of the walk discrimination processing by the walk discrimination device. Hereinafter, detailed description of configurations and functions similar to those in the first example embodiment may be omitted.

Figure 10:
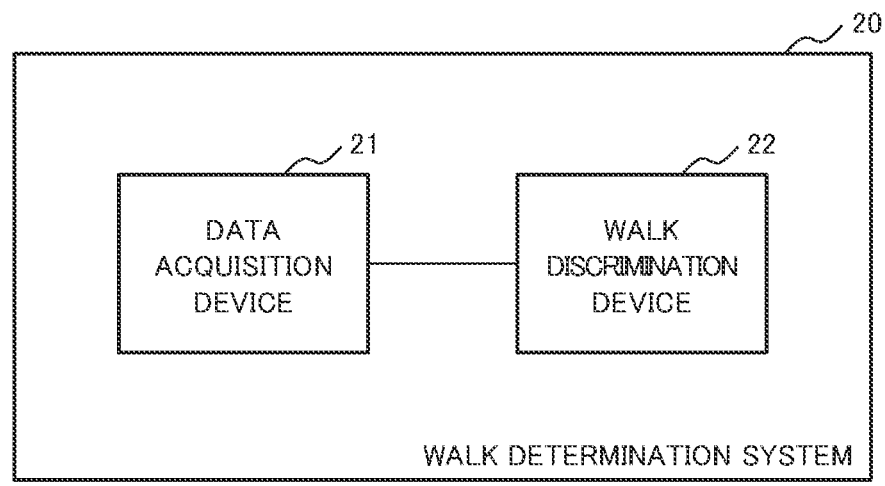
FIG. 10 is a block diagram illustrating an outline of a configuration of a walk determination system according to a second example embodiment of the present invention.

FIG. 10 is a block diagram illustrating an outline of a configuration of a walk determination system 20 of the present example embodiment. The walk determination system 20 includes a data acquisition device 21 and a walk discrimination device 22. Since main configurations and functions of the data acquisition device 21 and the walk discrimination device 22 are similar to those in the first example embodiment, detailed description thereof will be omitted. The walk determination system 20 of the present example embodiment is different from that of the first example embodiment in a part of the walk discrimination processing by the walk discrimination device 22.

The walk discrimination device 22 discriminates whether one step of walk has been performed on the basis of an order of receiving an over-threshold signal, a negative peak signal, a positive signal, a negative signal, and a positive peak signal. At this time, the walk discrimination device 22 determines that one step of walk has been performed in a case where the negative peak signal, the positive signal, the negative signal, and the positive peak signal are sequentially received within a predetermined time after the over-threshold signal is received.

For example, the walk discrimination device 22 receives the negative peak signal within a first predetermined time ($dT_1$) after receiving the over-threshold signal. Next, the walk discrimination device 22 receives the positive signal within a second predetermined time ($dT_2$) after receiving the negative peak signal. Next, the walk discrimination device 22 receives the negative signal within a third predetermined time ($dT_3$) after receiving the positive signal. Then, the walk discrimination device 22 receives the positive peak signal within a fourth predetermined time ($dT_4$) after receiving the negative signal. As described above, the walk discrimination device 22 determines that one step of walk has been performed in a case where the negative peak signal, the positive signal, the negative signal, and the positive peak signal are sequentially received within the predetermined time of each of the signals. For example, the walk discrimination device 22 manages a time until each of the over-threshold signal, the negative peak signal, the positive signal, the negative signal, and the positive peak signal is received on the basis of a time measured by a timer (not illustrated).

The predetermined time may be set for each of the negative peak signal, the positive signal, the negative signal, and the positive peak signal can be set in advance on the basis of a theoretical value or an experimental value of walking. Furthermore, the predetermined time may be set for each of the negative peak signal, the positive signal, the negative signal, and the positive peak signal may be set for each user. In addition, the walk discrimination device 22 may be configured to determine that a walk has not been performed at a time point when a predetermined time has passed since the reception of the over-threshold signal instead of the predetermined time set for each of the negative peak signal, the positive signal, the negative signal, and the positive peak signal.

[Walk Discrimination Processing]

Figure 11:
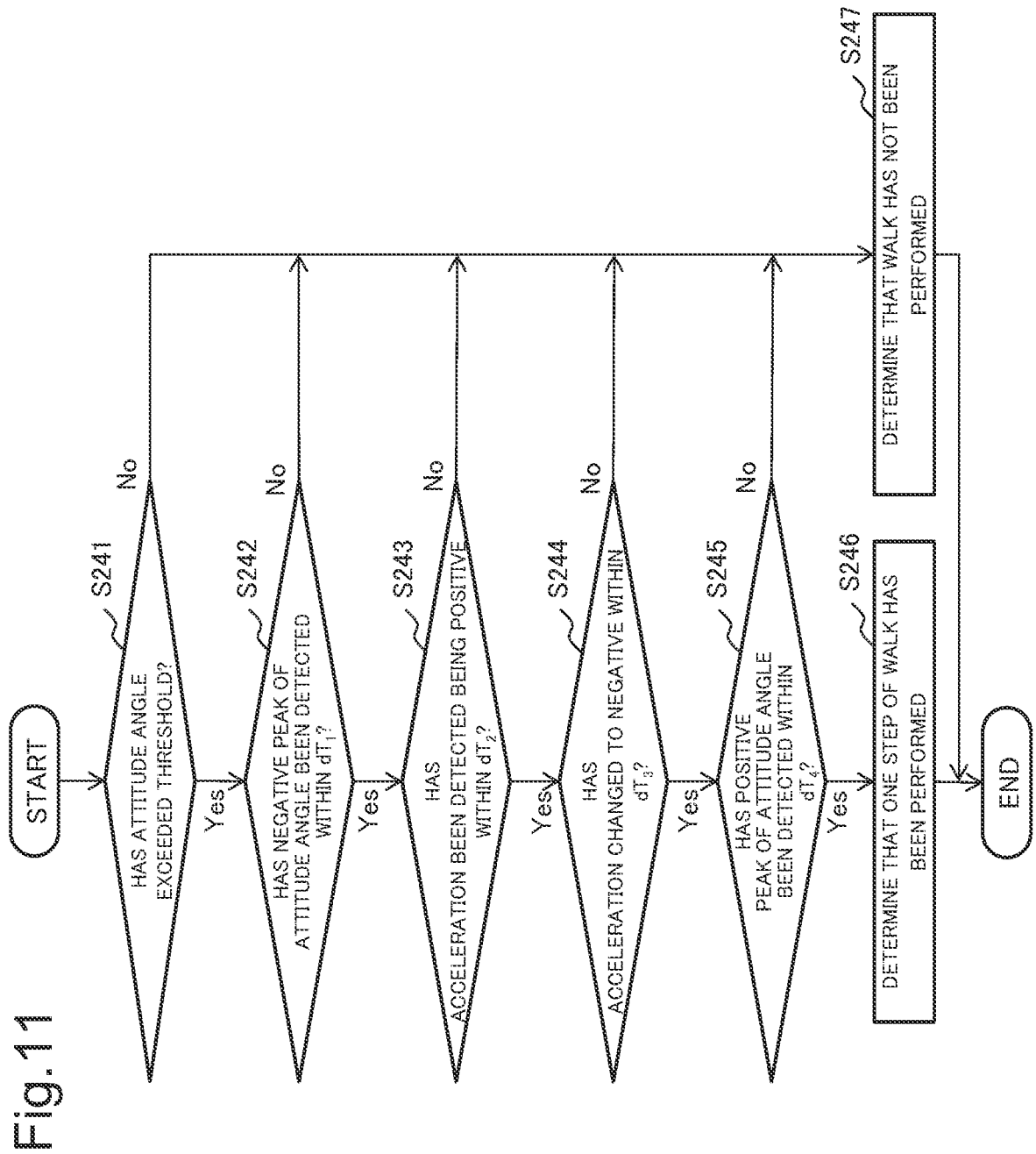
FIG. 11 is a flowchart for describing walk discrimination processing by a walk discrimination device included in the walk determination system according to the the second example embodiment of the present invention.

Next, the walk discrimination processing by the walk discrimination device 22 of the present example embodiment will be described with reference to FIG. 11. FIG. 11 is a flowchart for describing the walk discrimination processing by the walk discrimination device 22.

In FIG. 11, first, the walk discrimination device 22 determines whether an attitude angle has exceeded a threshold (step S241). If the attitude angle exceeds the threshold (Yes in step S241), the processing proceeds to step S242. On the other hand, if the attitude angle does not exceed the threshold (No in step S241), the walk discrimination device 22 determines that a walk has not been performed (step S247).

Next, the walk discrimination device 22 determines whether a negative peak of the attitude angle has been detected within the first predetermined time ($dT_1$) (step S242). If the negative peak of the attitude angle is detected within the first predetermined time ($dT_1$) (Yes in step S242), the processing proceeds to step S243. On the other hand, if the negative peak of the attitude angle is not detected within the first predetermined time ($dT_1$) (No in step S242), the walk discrimination device 22 determines that a walk has not been performed (step S247).

Next, the walk discrimination device 22 determines whether an acceleration has been detected being positive within the second predetermined time ($dT_2$) (step S243). If the acceleration is detected being positive within the second predetermined time ($dT_2$) (Yes in step S243), the processing proceeds to step S244. On the other hand, if the acceleration is not detected being positive within the second predetermined time ($dT_2$) (No in step S243), the walk discrimination device 22 determines that a walk has not been performed (step S247).

Next, the walk discrimination device 22 determines whether the acceleration has changed to negative within the third predetermined time ($dT_3$) (step S244). If the acceleration has changed to negative within the third predetermined time ($dT_3$) (Yes in step S244), the processing proceeds to step S245. On the other hand, if the acceleration does not change to negative within the third predetermined time ($dT_3$) (No in step S244), the walk discrimination device 22 determines that a walk has not been performed (step S247).

Next, the walk discrimination device 22 determines whether a positive peak of the attitude angle has been detected within the fourth predetermined time ($dT_4$) (step S245). If the positive peak of the attitude angle is detected within the fourth predetermined time ($dT_4$) (Yes in step S245), the walk discrimination device 22 determines that one step of walk has been performed (step S246). On the other hand, if the positive peak of the attitude angle is not detected within the fourth predetermined time ($dT_4$) (No in step S245), the walk discrimination device 22 determines that a walk has not been performed (step S247).

The walk discrimination processing by the walk discrimination device 22 has been described above. Note that the processing along the flowchart of FIG. 11 is an example, and the walk discrimination processing by the walk discrimination device 22 of the present example embodiment is not limited to this procedure as it is.

As described above, a walk determination system of the present example embodiment includes a walk discrimination device including a data reception unit, an acceleration determination unit, an attitude angle calculation unit, an attitude angle determination unit, a walk discrimination unit, and an output unit. The data reception unit receives sensor data including an acceleration and an angular velocity acquired by a sensor installed in a shoe. The acceleration determination unit determines whether the acceleration included in the sensor data is positive or negative. The attitude angle calculation unit calculates an attitude angle using the acceleration and the angular velocity included in the sensor data. The attitude angle determination unit determines whether the attitude angle calculated by the attitude angle calculation unit has exceeded a threshold, and determines whether a peak of the attitude angle has been detected. The walk discrimination unit discriminates a walk on the basis of a determination order by the acceleration determination unit and the attitude angle determination unit. The output unit outputs a discrimination result by the walk discrimination unit.

In one aspect of the present example embodiment, the walk discrimination unit determines that one step of walk has been performed in response to a receipt of a first attitude angle signal, a first acceleration signal, a second acceleration signal, and a second attitude angle signal within a predetermined time after receiving an over-threshold signal.

In addition, in one aspect of the present example embodiment, the walk discrimination unit determines that one step of walk has been performed in response to a sequential receipt of a negative peak signal, a positive signal, a negative signal, and a positive peak signal within a predetermined time of each of the signals after receiving the over-threshold signal. For example, the walk discrimination unit determines that one step of walk has been performed in response to a sequential receipt the first attitude angle signal within a first predetermined time, the first acceleration signal within a second predetermined time, the second acceleration signal within a third predetermined time, and the second attitude angle signal within a fourth predetermined time after receiving the over-threshold signal.

As described above, in the present example embodiment, it is determined that one step of walk has been performed in response to the sequential receipt of predetermined signals within the predetermined times after receiving the over-threshold signal. On the other hand, in the present example embodiment, it is determined that a walk has not been performed in a case where the predetermined signals are not sequentially received within the predetermined times after receiving the over-threshold signal. Therefore, according to the present example embodiment, it is possible to detect an abnormality in the received signals in a case where the first attitude angle signal, the first acceleration signal, the second acceleration signal, and the second attitude angle signal are not received for a long time after receiving the over-threshold signal. In addition, according to the present example embodiment, it is possible to distinguish and determine a slow walk, a quick walk, a run, and the like depending on a manner of setting the predetermined times.

(Hardware)

Here, a hardware configuration for executing the processing of the walk discrimination device according to each example embodiment of the present invention will be described using an information processing apparatus 90 in FIG. 12 as an example. Note that the information processing apparatus 90 in FIG. 12 is a configuration example for executing the processing of the walk discrimination device of each example embodiment, and does not limit the scope of the present invention.

Figure 12:
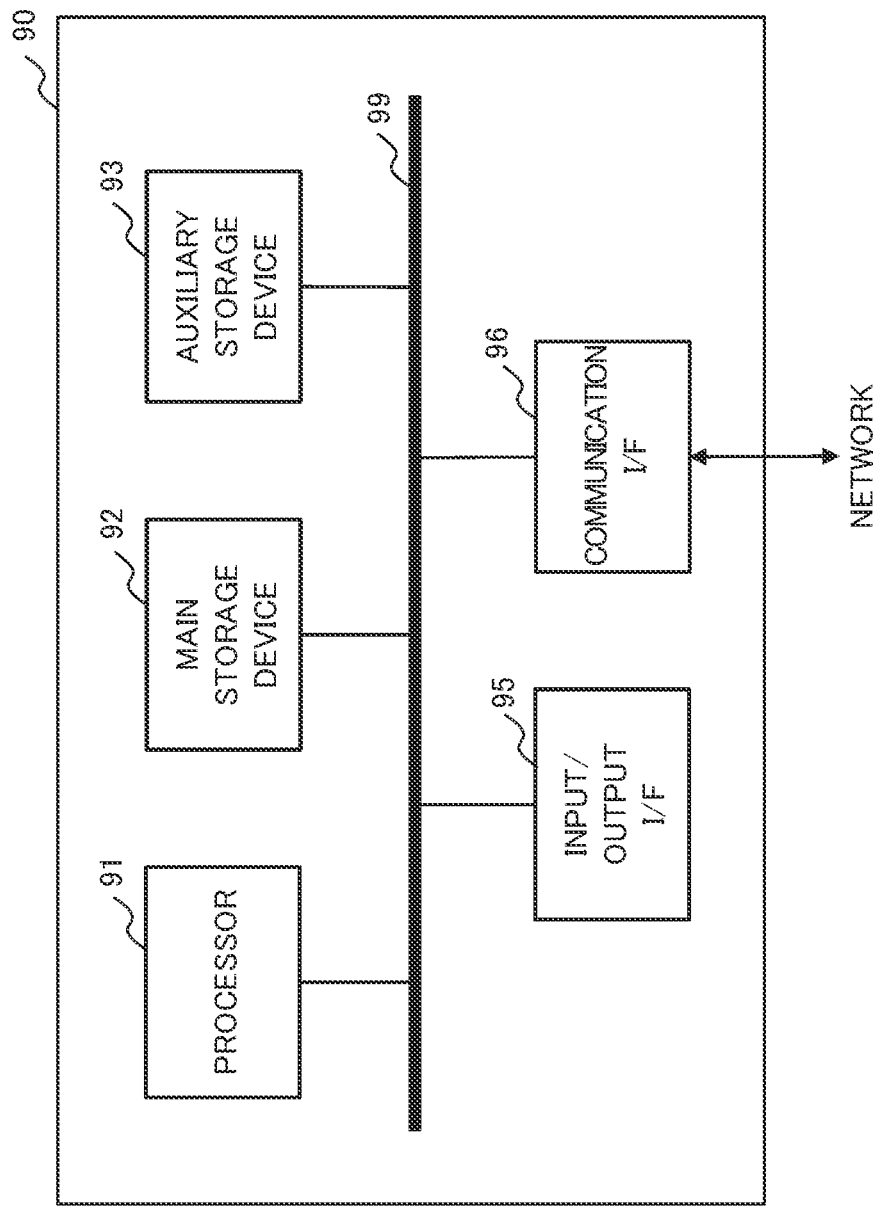
FIG. 12 is a block diagram illustrating an example of a hardware configuration for implementing the walk discrimination device included in the walk determination system according to each example embodiment of the present invention.

As illustrated in FIG. 12, the information processing apparatus 90 includes a processor 91, a main storage device 92, an auxiliary storage device 93, an input/output interface 95, and a communication interface 96. In FIG. 12, the interface is abbreviated as I/F (interface). The processor 91, the main storage device 92, the auxiliary storage device 93, the input/output interface 95, and the communication interface 96 are connected to each other via a bus 99 so as to enable data communication. In addition, the processor 91, the main storage device 92, the auxiliary storage device 93, and the input/output interface 95 are connected to a network such as the Internet or an intranet via the communication interface 96.

The processor 91 develops a program stored in the auxiliary storage device 93 or the like in the main storage device 92 and executes the developed program. In the present example embodiment, a software program installed in the information processing apparatus 90 can be used. The processor 91 executes the processing by the walk discrimination device according to the present example embodiment.

The main storage device 92 has an area in which the program is developed. The main storage device 92 can be a volatile memory such as a dynamic random access memory (DRAM), for example. In addition, a nonvolatile memory such as a magnetoresistive random access memory (MRAM) may be configured or added as the main storage device 92.

The auxiliary storage device 93 stores various types of data. The auxiliary storage device 93 includes a local disk such as a hard disk or a flash memory. Note that various types of data may be stored in the main storage device 92, so that the auxiliary storage device 93 can be omitted.

The input/output interface 95 is an interface for connecting the information processing apparatus 90 and a peripheral device. The communication interface 96 is an interface for connecting to an external system or device through a network such as the Internet or an intranet in accordance with a standard or a specification. The input/output interface 95 and the communication interface 96 may be shared as an interface for connecting to an external device.

An input device such as a keyboard, a mouse, or a touch panel may be connected to the information processing apparatus 90 as necessary. These input devices are used to input information or settings. In a case where the touch panel is used as the input device, a display screen of a display device can also serve as an interface of the input device. Data communication between the processor 91 and the input device can be mediated by the input/output interface 95.

Furthermore, the information processing apparatus 90 may be provided with a display device for displaying information. In a case where the display device is provided, the information processing apparatus 90 preferably includes a display control device (not illustrated) for controlling display of the display device. The display device can be connected to the information processing apparatus 90 via the input/output interface 95.

Furthermore, the information processing apparatus 90 may be provided with a disk drive as necessary. The disk drive is connected to the bus 99. The disk drive mediates, between the processor 91 and a recording medium (program recording medium) (not illustrated), reading of data and a program from the recording medium, writing of a processing result of the information processing apparatus 90 to the recording medium, and the like. The recording medium can be implemented by, for example, an optical recording medium such as a compact disc (CD) or a digital versatile disc (DVD). Furthermore, the recording medium may be implemented by a semiconductor recording medium such as a universal serial bus (USB) memory or a secure digital (SD) card, a magnetic recording medium such as a flexible disk, or another recording medium.

The above is the example of the hardware configuration for enabling the walk discrimination device according to each example embodiment of the present invention. Note that the hardware configuration in FIG. 12 is an example of the hardware configuration for executing the arithmetic processing of the walk discrimination device according to each example embodiment, and does not limit the scope of the present invention. In addition, a program for causing a computer to execute the processing related to the walk discrimination device according to each example embodiment is also included in the scope of the present invention. Furthermore, a program recording medium in which the program according to each example embodiment is recorded is also included in the scope of the present invention.

The components of the walk discrimination device of each example embodiment allow any combination. The components of the walk discrimination device of each example embodiment may be implemented by software or may be implemented by a circuit.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention.

REFERENCE SIGNS LIST 10, 20 Walk determination system
11, 21 Data acquisition device
12, 22 Walk discrimination device
111 Acceleration sensor
112 Angular velocity sensor
113 Signal processing unit
114 Data transmission unit
121 Data reception unit
122 Acceleration determination unit
123 Attitude angle calculation unit
124 Attitude angle determination unit
125 Timer
126 Walk discrimination unit
127 Output unit

What is claimed is:

1. A walk discrimination device comprising:
at least one memory storing instructions; and
at least one processor connected to the at least one memory and configured to execute the instructions to:
receive sensor data including an acceleration and an angular velocity acquired by a sensor installed in a shoe of a user;
calculate an attitude angle by use of the acceleration and the angular velocity included in the sensor data;
in response to the attitude angle exceeding a threshold, start a walk determination process based on a determination order that detecting a negative peak in the attitude angle, changing the acceleration to positive, changing the acceleration to negative, and detecting a positive peak in the attitude angle in this order;
when the determination order is satisfied, determine that the user is walking;
when the determination order is not satisfied, determine that the user is not walking;
output a first acceleration signal in response to the acceleration included in the sensor data is positive, and output a second acceleration signal in response to the acceleration included in the sensor data is negative, output an over-threshold signal in response to the attitude angle exceeding the threshold, output a first attitude angle signal in response to a detection of a negative peak of the attitude angle, output a second attitude angle signal in response to a detection of a positive peak of the attitude angle, and
determine that a walk has been performed in response to a sequential receipt of the first attitude angle signal, the first acceleration signal, the second acceleration signal, and the second attitude angle signal after receiving the over-threshold signal and the second attitude angle signal after receiving the over-threshold signal; and
output information including a discrimination result indicating whether the user is walking or not.

2. The walk discrimination device according to claim 1, wherein the at least one processor is configured to execute the instructions to determine that one step of walk has been performed in response to a sequential receipt of the first attitude angle signal, the first acceleration signal, the second acceleration signal, and the second attitude angle signal after receiving the over-threshold signal.

3. The walk discrimination device according to claim 1, further comprising a timer that supplies time data, wherein the at least one processor is configured to execute the instructions to discriminate an order of the first attitude angle signal, the first acceleration signal, the second acceleration signal, and the second attitude angle signal based on the time data supplied by the timer.

4. The walk discrimination device according to claim 1, wherein the at least one processor is configured to execute the instructions to determine one step of walk has been performed in response to a sequential receipt of the first attitude angle signal, the first acceleration signal, the second acceleration signal, and the second attitude angle signal within a predetermined time after receiving the over-threshold signal, and determine that a walk has not been performed in other cases.

5. The walk discrimination device according to claim 1, wherein, the at least one processor is configured to execute the instructions to determine that one step of walk has been performed in response to a sequential receipt of the first attitude angle signal within a first predetermined time, the first acceleration signal within a second predetermined time, the second acceleration signal within a third predetermined time, and the second attitude angle signal within a fourth predetermined time after receiving the over-threshold signal, and determine that a walk has not been performed in other cases.

6. A walk determination system comprising:
the walk discrimination device according to claim 1; and
a data acquisition device that is installed in a shoe, includes a sensor, detects the acceleration and the angular velocity, generates the sensor data including the detected acceleration and the detected angular velocity, and transmits the generated sensor data to the walk discrimination device.

7. A walk discrimination method comprising:
receiving sensor data including an acceleration and an angular velocity acquired by a sensor installed in a shoe of a user;
calculating an attitude angle by use of the acceleration and the angular velocity included in the sensor data;
in response to the attitude angle exceeding a threshold, starting a walk determination process based on a determination order that detecting a negative peak in the attitude angle, changing the acceleration to positive, changing the acceleration to negative, and detecting a positive peak in the attitude angle in this order;
when the determination order is satisfied, determining that the user is walking; when the determination order is not satisfied, determining that the user is not walking;
outputting a first acceleration signal in response to the acceleration included in the sensor data is positive, and outputting a second acceleration signal in response to the acceleration included in the sensor data is negative, outputting an over-threshold signal in response to the attitude angle exceeding the threshold, outputting a first attitude angle signal in response to a detection of a negative peak of the attitude angle, outputting a second attitude angle signal in response to a detection of a positive peak of the attitude angle,
determining that a walk has been performed in response to a sequential receipt of the first attitude angle signal, the first acceleration signal, the second acceleration signal, and the second attitude angle signal after receiving the over-threshold signal and the second attitude angle signal after receiving the over-threshold signal; and outputting information including a discrimination result indicating whether the user is walking or not.

8. A non-transient program recording medium recording a program for causing a computer to execute:

processing of receiving sensor data including an acceleration and an angular velocity acquired by a sensor installed in a shoe of a user;

processing of calculating an attitude angle by use of the acceleration and the angular velocity included in the sensor data;

in response to the attitude angle exceeding a threshold, processing of starting a walk determination process based on a determination order that detecting a negative peak in the attitude angle, changing the acceleration to positive, changing the acceleration to negative, and detecting a positive peak in the attitude angle in this order;

when the determination order is satisfied, processing of determining that the user is walking; when the determination order is not satisfied, processing of determining that the user is not walking;

processing of outputting a first acceleration signal in response to the acceleration included in the sensor data is positive, and processing of outputting a second acceleration signal in response to the acceleration included in the sensor data is negative, processing of outputting an over-threshold signal in response to the attitude angle exceeding the threshold, processing of outputting a first attitude angle signal in response to a detection of a negative peak of the attitude angle, processing of outputting a second attitude angle signal in response to a detection of a positive peak of the attitude angle, processing of determining that a walk has been performed in response to a sequential receipt of the first attitude angle signal, the first acceleration signal, the second acceleration signal, and the second attitude angle signal after receiving the over-threshold signal and the second attitude angle signal after receiving the over-threshold signal; and processing of outputting information including a discrimination result indicating whether the user is walking or not.

* * * * *